United States Patent
Liu et al.

(10) Patent No.: US 10,351,499 B2
(45) Date of Patent: Jul. 16, 2019

(54) METHODS FOR PRODUCING SOLVENTS DERIVED FROM 1-CHLORO-3, 3, 3-TRIFLUORO-PROPENE (1233ZD)

(71) Applicant: Honeywell International Inc., Morris Plains, NJ (US)

(72) Inventors: Ya Qun Liu, Shanghai (CN); Hong Min Huang, Shanghai (CN); Jun Liu, Shanghai (CN); Rajiv R. Singh, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 17 days.

(21) Appl. No.: 15/606,400

(22) Filed: May 26, 2017

(65) Prior Publication Data
US 2017/0349519 A1    Dec. 7, 2017

Related U.S. Application Data

(60) Provisional application No. 62/345,117, filed on Jun. 3, 2016.

(51) Int. Cl.
| | |
|---|---|
| C07C 41/01 | (2006.01) |
| C10M 131/10 | (2006.01) |
| C09K 21/06 | (2006.01) |
| C09K 3/30 | (2006.01) |
| C09K 13/00 | (2006.01) |
| A62D 1/00 | (2006.01) |
| C09K 3/00 | (2006.01) |
| C09K 5/04 | (2006.01) |
| C11D 3/43 | (2006.01) |
| C07C 41/06 | (2006.01) |
| C07C 41/24 | (2006.01) |
| C11D 7/50 | (2006.01) |
| A61D 1/00 | (2006.01) |

(52) U.S. Cl.
CPC ............ *C07C 41/01* (2013.01); *A62D 1/0028* (2013.01); *A62D 1/0057* (2013.01); *C07C 41/06* (2013.01); *C07C 41/24* (2013.01); *C09K 3/00* (2013.01); *C09K 3/30* (2013.01); *C09K 5/044* (2013.01); *C09K 5/045* (2013.01); *C09K 13/00* (2013.01); *C09K 21/06* (2013.01); *C10M 131/10* (2013.01); *C11D 3/43* (2013.01); *C11D 7/5018* (2013.01); *C09K 2205/112* (2013.01); *C09K 2205/24* (2013.01)

(58) Field of Classification Search
None
See application file for complete search history.

(56) References Cited

U.S. PATENT DOCUMENTS

| | | |
|---|---|---|
| 2,739,987 A | 3/1956 | Rah |
| 5,777,184 A | 7/1998 | Van Der Puy et al. |
| 6,111,139 A | 8/2000 | Van Der Puy |
| 7,544,844 B2 | 6/2009 | Komata et al. |
| 7,736,537 B1 | 6/2010 | Zastrow et al. |
| 7,985,299 B2 | 7/2011 | Johnson et al. |
| 8,772,213 B2 | 7/2014 | DeCaire |
| 9,216,932 B2 | 12/2015 | Zhai et al. |
| 9,303,162 B2 | 4/2016 | Bowman et al. |
| 2007/0105044 A1* | 5/2007 | Maeda ................ G03F 7/0046 430/270.1 |
| 2009/0105506 A1 | 4/2009 | Komata et al. |
| 2009/0305876 A1 | 12/2009 | Singh et al. |
| 2010/0145112 A1* | 6/2010 | Ishihara ................ C07C 17/25 570/156 |
| 2011/0041529 A1 | 2/2011 | Chen et al. |
| 2014/0179961 A1* | 6/2014 | Zhai ...................... C07C 17/25 570/156 |
| 2014/0315774 A1 | 10/2014 | Decaire et al. |
| 2014/0343330 A1* | 11/2014 | Zhai ...................... C07C 17/25 570/155 |

FOREIGN PATENT DOCUMENTS

| | | |
|---|---|---|
| CN | 102320938 B | 4/2014 |
| JP | 2006298855 A | 11/2006 |

OTHER PUBLICATIONS

International Search Report and Written Opinion issued in PCT/US2017/034953, dated Sep. 7, 2017, 18 pages.

* cited by examiner

*Primary Examiner* — Joseph D Anthony
(74) *Attorney, Agent, or Firm* — Faegre Baker Daniels LLP

(57) ABSTRACT

The production of solvents for applications such as heat transfer, cleaning, and degreasing, for example. In particular, the production of solvents derived from 1-chloro-3,3,3-trifluoro-propene, such as chloro and/or fluoro substituted alkanes and chloro and/or fluoro substituted trifluoropropenyl ethers.

16 Claims, No Drawings

METHODS FOR PRODUCING SOLVENTS DERIVED FROM 1-CHLORO-3,3,3-TRIFLUORO-PROPENE (1233ZD)

CROSS REFERENCE TO RELATED APPLICATIONS

This application claims the benefit under Title 35, U.S.C. §119(e) of U.S. Provisional Patent Application Ser. No. 62/345,117, entitled METHODS FOR PRODUCING SOLVENTS DERIVED FROM 1-CHLORO-3,3,3-TRIFLUORO-PROPENE (1233zd), filed on Jun. 3, 2016, the entire disclosure of which is expressly incorporated by reference herein.

BACKGROUND

The present disclosure relates to the production of solvents for use in applications such as heat transfer, cleaning and degreasing, for example and, in particular, the present disclosure relates to the production of solvents that are derived from 1-chloro-3,3,3-trifluoro-propene.

1-chloro-3,3,3-trifluoro-propene ($CF_3CH=CHCl$, also known as 1233zd) may be used as heat transfer fluid, as well as a cleaning solvent or a carrier solvent. Advantageously, 1233zd is non-flammable, has a low global warming potential (GWP), and low toxicity. 1233zd is also an effective solvent for a number of organic substances, such as different kinds of oils and greases, making 1233zd useful as a cleaning and degreasing solvent.

However, because 1233zd has a low boiling point (19° C. for the trans isomer), when 1233zd is used as a solvent, challenges are presented in connection with handling and operation. For example, 1233zd is typically transported and dispensed from a high pressure cylinder package, which may be costly and may require complex process integration steps with existing machinery and tooling, as well as training of personnel. The low boiling point of 1233zd may also result in higher vapor loss, potentially leading to a higher rate of consumption. In addition to potential challenges relating to the low boiling point of 1233zd, there is some concern in certain use applications regarding the chlorine atom in the molecule, for example, in the electronics manufacturing industry where halogen-free reagents and solvents may be desired.

Solvents based on 1233zd which exhibit one or more of the properties of non-chlorine containing, low GWP, low toxicity, and non-flammability are desired.

SUMMARY

The present disclosure relates to the production of solvents for applications such as heat transfer, cleaning, and degreasing, for example. In particular, the present disclosure relates to the production of solvents derived from 1-chloro-3,3,3-trifluoro-propene, such as chloro and/or fluoro substituted alkanes and chloro and/or fluoro substituted trifluoropropenyl ethers.

In one form thereof, the present disclosure provides a method for producing a product according to one of formulas:

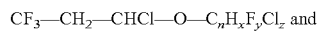

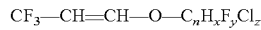

wherein:
n is 1 to 5;
x, y, and z are each 0 to 11 and y+z 1; and
x+y+z=2(n−m)+1, wherein m is an integer of 0 to 2, the method comprising the step of reacting a reaction mixture including an alcohol, a catalyst, and 1-chloro-3,3,3-trifluoro-propene (1233zd).

The alcohol may be an alcohol according to the following formula:

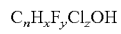

wherein:
n is 1 to 5;
x, y, and z are each 0 to 11 and y+z 1; and
x+y+z=2n+1 for a saturated alcohol; or
x+y+z=2n−1 for an unsaturated alcohol.

The alcohol may be selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

The catalyst may be an alkaline catalyst and, in particular, may include at least one alkali hydroxide selected from the group consisting of sodium hydroxide and potassium hydroxide and a combination thereof.

The method may further include, after the reacting step, the additional step of separating the product of from the reaction mixture. The reacting step may further include heating the reaction mixture. The reacting step may further include the additional steps of: mixing the alcohol and the catalyst in a reaction vessel; and after the mixing step, adding 1-chloro-3,3,3-trifluoro-propene (1233zd) to the reaction vessel.

The 1-chloro-3,3,3-trifluoro-propene (1233zd) may be either the trans isomer of 1-chloro-3,3,3-trifluoro-propene (1233zd) or the cis isomer of 1-chloro-3,3,3-trifluoro-propene (1233zd).

The product of the method may have the following formula:

wherein:
n is 1 to 5;
x, y, and z are each 0 to 11 and y+z 1; and
x+y+z=2(n−m)+1, wherein m is an integer of 0 to 2, said method comprising the step of reacting a reaction mixture including an alcohol, a catalyst, and 1-chloro-3,3,3-trifluoro-propene (1233zd).

The alcohol may be an alcohol according to the following formula:

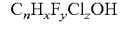

wherein:
n is 1 to 5;
x, y, and z are each 0 to 11 and y+z 1; and
x+y+z=2n+1 for a saturated alcohol; or
x+y+z=2n−1 for an unsaturated alcohol.

The alcohol may be selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

The product of the method may have the following formula:

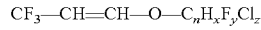

wherein:

n is 1 to 5;

x, y, and z are each 0 to 11 and y+z 1; and x+y+z=2(n−m)+1, wherein m is an integer of 0 to 2, said method comprising the step of reacting a reaction mixture including an alcohol, a catalyst, and 1-chloro-3,3,3-trifluoro-propene (1233zd).

The alcohol may be an alcohol according to the following formula:

wherein:

n is 1 to 5;

x, y, and z are each 0 to 11 and y+z 1; and x+y+z=2n+1 for a saturated alcohol; or x+y+z=2n−1 for an unsaturated alcohol.

The alcohol may be selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

In another form thereof, the present disclosure provides a liquid composition including at least one solvent selected from formulas (I) and (II):

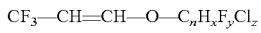

and combinations thereof, wherein:

n is 1 to 5;

x, y, and z are each 0 to 11 and y+z 1; and x+y+z=2(n−m)+1, wherein m is an integer of 0 to 2, said method comprising the step of reacting a reaction mixture including an alcohol, a catalyst, and 1-chloro-3,3,3-trifluoro-propene (1233zd); and at least one solvent having a boiling point between 20-250° C.

The solvent may have a boiling pint between 20-100° C. or between 25-70° C., and at least one solvent may have an ozone depletion potential (ODP) of not greater than about 0.5.

DETAILED DESCRIPTION

The present disclosure relates to the production of solvents for applications such as heat transfer, cleaning, and degreasing, for example. In particular, the present disclosure relates the production of solvents derived from 1-chloro-3,3,3-trifluoro-propene, such as chloro and/or fluoro substituted alkanes and chloro and/or fluoro substituted trifluoropropenyl ethers.

1-chloro-3,3,3-trifluoro-propene, $CF_3CH=CHCl$, also known as 1233zd, is a non-flammable, low GWP, low toxicity solvent. The chemical structure of 1233zd is set forth in formula (I) below:

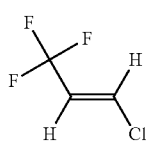

1233zd exists as a trans isomer, as shown in formula (I) above, in which the $CF_3$ and Cl groups are on opposite sides of the double bond with respect to the longest chain of carbon atoms, and as a cis isomer, shown formula (II) below, in which the $CF_3$ and Cl groups are on the same side of the double bond with respect to the longest chain of carbon atoms:

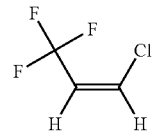

The trans isomer has a boiling point of 19° C., while the cis isomer has a boiling point of 40° C.

In order to form useful solvents derived from 1233zd, the 1233zd starting material is reacted with an alcohol and a catalyst according to the overall reaction (1) below, in which the alcohol is exemplified as fluoromethanol ($CH_2FOH$) and the catalyst is exemplified as potassium hydroxide:

$$CF_3CH=CHCl+CH_2FOH+KOH \rightarrow CF_3CH=CH-O-CH_2F+KCl+H_2O \quad (1)$$

Suitable alcohols for use with the present methods may be generally described by the following chemical formula:

wherein:

n is 1 to 5;

x, y, and z are each 0 to 11, and y+z 1; and x+y+z=2n+1 for a saturated alcohol; or x+y+z=2n−1 for an unsaturated alcohol.

In exemplary embodiments, the alcohol may be a chloro-alcohol, a fluoro-alcohol, or a chloro/fluoro-alcohol, having constituent carbons are at least partially substituted with chlorine, fluorine, or both chlorine and fluorine atoms. Exemplary fluoro-alcohols include, e.g., fluoromethanol ($CH_2FOH$), 2,2,2-trifluoroethanol ($CF_3CH_2OH$), 3,3,3-trifluoro-1-propanol ($CF_3CH_2CH_2OH$), 2,2,3,3-tetrafluoro-1-propanol ($CHF_2CF_2CH_2OH$), 2,2,3,3,4,4,5,5-octafluoropentanol ($CHF_2CF_2CF_2CF_2CH_2OH$), and 1,1,1,3,3,3-hexafluoro-propan-2-ol ($(CF_3)_2CHOH$).

The alcohol functions as a solvent for the reaction, and as a chlorine substituent to replace the chlorine atom of 1233zd to form an alkoxy group.

The catalyst may be an alkaline catalyst, such as an alkali hydroxide including, for example, sodium hydroxide (NaOH) and/or potassium hydroxide (KOH), and functions in part to absorb the chlorine atom which is removed from 1233zd.

In one exemplary embodiment, the molar ratio of 1233zd to alcohol may be 10:1 to 1:20 and the molar ratio of 1233zd to catalyst may be 100:1 to 1:5. In one particular embodiment, the molar ratio of 1233zd to alcohol to catalyst is about 1:4:1.2.

The reaction may be initiated by first combining the catalyst and the alcohol in a reaction vessel, such as an autoclave, with stirring, followed by adding the 1233zd to the reaction vessel with continued stirring.

In a first stage addition reaction, set forth as reaction (2) below and again exemplified in connection with fluoromethanol as the alcohol, the alcohol adds across the double bond of 1233zd, typically with high selectivity for the addition of the alcohol to the number 3 carbon opposite the double bond from the $CF_3$ group, to form an intermediate alkane:

$$CF_3CH=CHCl+CH_2FOH \rightarrow CF_3CH_2CHCl-OCH_2F \quad (2)$$

Depending on the alcohol used, the carbon(s) of the intermediate alkane may be substituted with chlorine, fluorine, or both chlorine and fluorine. Reaction (2) is exothermic and typically spontaneous, and a cooling medium may be employed during the reaction, such as a cold water bath, for example, or the reaction may be conducted in a cooled environment.

The products of the first stage addition reaction themselves could be final products used as solvents for various applications according to the present disclosure, wherein such products will have molecular weights and boiling points higher than that of 1233zd, the boiling points typically higher than 40° C.

The alkane intermediate products of the first stage addition reaction may be described by the following chemical formula:

$CF_3$—$CH_2$—$CHCl$—O—$C_nH_xF_yCl_z$ wherein:

n is 1 to 5;

x, y, and z are each 0 to 11 and y+z 1; and x+y+z=2(n−m)+1, wherein m is an integer of 0 to 2.

In a second stage elimination (or dehydrohalogenation) reaction following reaction (2), set forth as reaction (3) below and again exemplified in connection with fluoromethanol as the alcohol and potassium hydroxide as the catalyst, a trifluoropropene ether is produced when the alkane intermediate loses the chlorine atom and a hydrogen atom to re-form the double bond between the number 2 and 3 carbons:

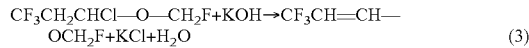

$CF_3CH_2CHCl$—O—$CH_2F$+$KOH$→$CF_3CH$=$CH$—$OCH_2F$+$KCl$+$H_2O$     (3)

Thus, in the exemplary reaction (3) above, 3,3,3-triflulo-ropropenyl fluoromethyl ether is formed which, along with other products disclosed herein, will have molecular weights and boiling points higher than that of 1233zd, the boiling points typically higher than 40° C.

Reaction (3) above is endothermic and, in one embodiment, the reaction vessel may be heated as needed to initiate and/or perpetuate the reaction.

Again, depending on the alcohol used, the number of carbon(s) of the trifluoropropene ether may vary, and may be substituted with chlorine, fluorine, or both chlorine and fluorine.

The trifluoropropene ether products of the second stage elimination reaction may be described by the following chemical formula:

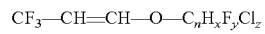

$CF_3$—$CH$=$CH$—O—$C_nH_xF_yCl_z$ wherein:

n is 1 to 5;

x, y, and z are each 0 to 11 and y+z 1; and x+y+z=2(n−m)+1, wherein m is an integer of 0 to 2.

The products of the first and second stage reactions may be separated from the reaction mixture and/or other products by suitable means depending on their chemical structure and/or boiling point, such as filtration, extraction with water or other solvent and/or distillation, such as atmospheric distillation and/or reduced pressure distillation, for example.

Several exemplary alcohols, together with their resulting first and second stage reaction products that may be obtained in accordance with the present disclosure, are set forth in the Table I below:

TABLE I

Exemplary alcohols and 1$^{st}$ and 2$^{nd}$ stage products

| Alcohol | 1$^{st}$ stage product (of reaction (2)) | 2$^{nd}$ stage product (of reaction (3)) |
|---|---|---|
| Fluoromethanol [$CH_2FOH$] (n = 1, x = 2, y = 1, z = 0) | 1-chloro-3,3,3-trifluoropropyl fluoromethyl ether or 1-chloro-1-fluoromethoxy-3,3,3-trifluoropropane [$CF_3CH_2CHCl$—$OCH_2F$] | 3,3,3-trifluoropropenyl fluoromethyl ether or 1-fluoromethoxy-3,3,3-trifluloropropene [$CF_3CH$=$CH$—$OCH_2F$] |
| Difluoromethanol [$CHF_2OH$] (n = 1, x = 1, y = 2, z = 0) | 1-chloro-3,3,3-trifluoropropyl difluoromethyl ether or 1-chloro-1-difluoromethoxy-3,3,3-trifluoropropane [$CF_3CH_2CHCl$—$OCHF_2$] | 3,3,3-trifluoropropenyl difluoromethyl ether or 1-difluoromethoxy-3,3,3-trifluloropropene [$CF_3CH$=$CH$—$OCHF_2$] |
| 2-fluoroethanol [$CH_2FCH_2OH$] (n = 2, x = 4, y = 1, z = 0) | 1-chloro-3,3,3-trifluoropropyl 2-fluoroethyl ether or 1-chloro-1-(2-fluoroethoxy)-3,3,3-trifluoropropane [$CF_3CH_2CHCl$—$OCH_2CH_2F$] | 3,3,3-trifluoropropenyl 2-fluoroethyl ether or 1-(2-fluoroethoxy)-3,3,3-trifluloropropene [$CF_3CH$=$CH$—$OCH_2CH_2F$] |
| 2,2-difluoroethanol [$CHF_2CH_2OH$] (n = 2, x = 3, y = 2, z = 0) | 1-chloro-3,3,3-trifluoropropyl 2,2-difluoroethyl ether or 1-chloro-1-(2,2-difluoroethoxy)-3,3,3-trifluoropropane [$CF_3CH_2CHCl$—$OCH_2CHF_2$] | 3,3,3-trifluoropropenyl 2,2-difluoroethyl ether or 1-(2,2-difluoroethoxy)-3,3,3-trifluloropropene [$CF_3CH$=$CH$—$OCH_2CHF_2$] |
| 2,2,2-trifluoroethanol [$CF_3CH_2OH$] (n = 2, x = 2, y = 3, z = 0) | 1-chloro-3,3,3-trifluoropropyl 2,2,2-trifluoroethyl ether | 3,3,3-trifluoropropenyl 2,2,2-trifluoroethyl ether or |

TABLE I-continued

Exemplary alcohols and 1st and 2nd stage products

| Alcohol | 1st stage product (of reaction (2)) | 2nd stage product (of reaction (3)) |
|---|---|---|
| | or<br>1-chloro-1-(2,2,2-trifluoroethoxy)-3,3,3-trifluoropropane [$CF_3CH_2CHCl-OCH_2CF_3$] | 1-(2,2,2-trifluoroethoxy)-3,3,3-trifluloropropene [$CF_3CH=CH-OCH_2CF_3$] |
| 2-fluoroallyl alcohol [$CH_2=CFCH_2OH$] (n = 3, x = 4, y = 1, z = 0) | 1-chloro-3,3,3-trifluoropropyl 2-fluoroallyl ether<br>or<br>1-chloro-1-(2-fluoroallyoxy)-3,3,3-trifluoropropane [$CF_3CH_2CHCl-OCH_2CH_2CH_2F$] | 3,3,3-trifluoropropenyl 2-fluoroallyl ether<br>or<br>1-(2-fluoroallyoxy)-3,3,3-trifluloropropene [$CF_3CH=CH-OCH_2CH_2CH_2F$] |
| 3-fluoro-1-propanol [$CH_2FCH_2CH_2OH$] (n = 3, x = 6, y = 1, z = 0) | 1-chloro-3,3,3-trifluoropropyl 3-fluoropropyl ether<br>or<br>1-chloro-1-(3-fluoropropoxy)-3,3,3-trifluoropropane [$CF_3CH_2CHCl-OCH_2CH_2CH_2F$] | 3,3,3-trifluoropropenyl 3-fluoropropyl ether<br>or<br>1-(3-fluoropropoxy)-3,3,3-trifluloropropene [$CF_3CH=CH-OCH_2CH_2CH_2F$] |
| 2,2-difluoro-1-propanol [$CH_3CF_2CH_2OH$] (n = 3, x = 5, y = 2, z = 0) | 1-chloro-3,3,3-trifluoropropyl 2,2-difluoropropyl ether<br>or<br>1-chloro-1-(2,2-difluoropropoxy)-3,3,3-trifluoropropane [$CF_3CH_2CHCl-OCH_2CF_2CH_3$] | 3,3,3-trifluoropropenyl 2,2-difluoropropyl ether<br>or<br>1-(2,2-difluoropropoxy)-3,3,3-trifluloropropene [$CF_3CH=CH-OCH_2CFS_2CH_3$] |
| 3,3,3-trifluoro-1-propanol [$CF_3CH_2CH_2OH$] (n = 3, x = 4, y = 3, z = 0) | 1-chloro-3,3,3-trifluoropropyl 3,3,3-trifluoropropyl ether<br>or<br>1-chloro-1-(3,3,3-trifluoropropoxy)-3,3,3-trifluoropropane [$CF_3CH_2CHCl-OCH_2CH_2CF_3$] | 3,3,3-trifluoropropenyl 3,3,3-trifluoropropyl ether<br>or<br>1-(3,3,3-trifluoropropoxy)-3,3,3-trifluloropropene [$CF_3CH=CH-OCH_2CH_2CF_3$] |
| 2,2,3,3-tetrafluoro-1-propanol [$CHF_2CF_2CH_2OH$] (n = 3, x = 3, y = 4, z = 0) | 1-chloro-3,3,3-trifluoropropyl 2,2,3,3-tetrafluoropropyl ether<br>or<br>1-chloro-1-(2,2,3,3-tetrafluoropropoxy)-3,3,3-trifluloropropene [$CF_3CH_2CHCl-OCH_2CF_2CHF_2$] | 3,3,3-trifluoropropenyl 2,2,3,3-tetrafluoropropyl ether<br>or<br>1-(2,2,3,3-tetrafluoropropoxy)-3,3,3-trifluoropropane [$CF_3CH=CH-OCH_2CF_2CHF_2$] |
| 2,2,3,3,3-pentafluoro-1-propanol [$CF_3CF_2CH_2OH$] (n = 3, x = 2, y = 5, z = 0) | 1-chloro-3,3,3-trifluoropropyl 2,2,3,3,3-pentafluoropropyl ether<br>or<br>1-chloro-1-(2,2,3,3,3-pentafluoropropoxy)-3,3,3-trifluoropropane [$CF_3CH_2CHCl-OCH_2CF_2CF_3$] | 3,3,3-trifluoropropenyl 2,2,3,3,3-pentafluoropropyl ether<br>or<br>1-(2,2,3,3,3-pentafluoropropoxy)-3,3,3-trifluloropropene [$CF_3CH=CH-OCH_2CF_2CF_3$] |
| 1,1,1,3,3,3-hexafluoro-2-propanol [$(CF_3)_2CHOH$] (n = 3, x = 1, y = 6, z = 0) | 1-chloro-3,3,3-trifluoropropyl 1,1,1,3,3,3-hexafluoroisopropyl ether<br>or<br>1-chloro-1-(1,1,1,3,3,3-hexafluoroisopoxy)-3,3,3-trifluloropropene [$CF_3CH_2CHCl-OCH(CF_3)_2$] | 3,3,3-trifluoropropenyl 1,1,1,3,3,3-hexafluoroisopropyl ether<br>or<br>1-(1,1,1,3,3,3-hexafluoroisopoxy)-3,3,3-trifluoropropane [$CF_3CH=CH-OCH(CF_3)_2$] |
| 2-chloro-1-ethanol [$CH_2ClCH_2OH$] (n = 2, x = 4, y = 0, z = 1) | 1-chloro-3,3,3-trifluoropropyl 2-chloroethyl ether<br>or<br>1-chloro-1-(2-chloroethoxy)-3,3,3-trifluoropropane [$CF_3CH_2CHCl-OCH_2CH_2Cl$] | 3,3,3-trifluoropropenyl vinyl ether<br>or<br>1-vinyloxy-3,3,3-trifluloropropene [$CF_3CH=CH-OCH=CH_2$] |
| 1,3-dichloro-2-propanol [$(CH_2Cl)_2CHOH$] (n = 3, x = 5, y = 0, z = 2) | 1-chloro-3,3,3-trifluoropropyl 1,3-dichloroisopropyl ether<br>or<br>1-chloro-1-(1,3-dichloroisopoxy)-3,3,3- | 3,3,3-trifluoropropenyl 1-chloromethylethenyl ether<br>or<br>1-(1-chloromethylethenyloxy)-3,3,3-trifluoropropene |

TABLE I-continued

Exemplary alcohols and 1st and 2nd stage products

| Alcohol | 1st stage product (of reaction (2)) | 2nd stage product (of reaction (3)) |
|---|---|---|
| | trifluoropropane [$CF_3CH_2CHCl$—$OCH(CH_2Cl)_2$] | [$CF_3CH$=$CH$—$OC(CH_2Cl)$=$CH_2$] |
| 2,2,3,4,4,4-hexafluorobutanol [$CF_3CHFCF_2CH_2OH$] (n = 4, x = 3, y = 6, z = 0) | 1-chloro-3,3,3-trifluoropropyl 2,2,3,4,4,4-hexafluorobutyl ether or 1-chloro-1-(3-fluoropropoxy)-2,2,3,4,4,4-hexafluorobutane [$CF_3CH_2CHCl$—$OCH_2CF_2CHFCF_3$] | 3,3,3-trifluoropropenyl 2,2,3,4,4,4-hexafluorobutyl ether or 3,3,3-trifluoropropenyloxy-2,2,3,4,4,4-hexafluorobutane [$CF_3CH$=$CH$—$OCH_2CF_2CHFCF_3$] |
| 2,2,3,3,4,4,4-heptafluorobutanol [$CF_3CF_2CF_2CH_2OH$] (n = 4, x = 2, y = 7, z = 0) | 1-chloro-3,3,3-trifluoropropyl 2,2,3,3,4,4,4-heptafluorobutyl ether or 1-chloro-1-(3-fluoropropoxy)-2,2,3,3,4,4,4-heptafluorobutane [$CF_3CH_2CHCl$—$OCH_2CF_2CF_2CF_3$] | 3,3,3-trifluoropropenyl 2,2,3,3,4,4,4-heptafluorobutyl ether or 3,3,3-trifluoropropenyloxy-2,2,3,3,4,4,4-heptafluorobutane [$CF_3CH$=$CH$—$OCH_2CF_2CHFCF_3$] |
| 2,2,3,3,4,4,5,5-octafluoropentanol [$CHF_2CF_2CF_2CF_2CH_2OH$] (n = 5, x = 2, y = 8, z = 0) | 1-chloro-3,3,3-trifluoropropyl 2,2,3,3,4,4,5,5-octafluoropentyl ether or 1-chloro-1-(3-fluoropropoxy)-2,2,3,3,4,4,5,5-octafluoropentane [$CF_3CH_2CHCl$—$OCH_2CF_2CF_2CF_2CHF_2$] | 3,3,3-trifluoropropenyl 2,2,3,3,4,4,5,5-octafluoropentyl ether or 3,3,3-trifluoropropenyloxy-2,2,3,3,4,4,5,5-octafluoropentane [$CF_3CH$=$CH$—$OCH_2CF_2CF_2CF_2CHF_2$] |

Advantageously, the products of the first and second stage reactions will have a higher molecular weight, and therefore a higher boiling point, than 1233zd and, in many cases, such products will have a boiling point higher than room temperature (between 15° C. and 25° C.), thereby facilitating use of the products as solvents in many potential applications.

The products of the first and second stage reactions, i.e., the disclosed compounds, exhibit one or more, and may exhibit all, of the following properties: chemical stability; no substantial ozone depleting potential (ODP); relatively high degree of miscibility with common contaminants, particularly mineral oil and/or silicone oil; low or no flammability; low or no toxicity; and low or no global warming potential (GWP).

More specifically, the disclosed compounds may have: no substantial ozone depletion potential, preferably an ODP of not greater than about 0.5, not greater than about 0.25, or not greater than about 0.1; a GWP of not greater than about 150, or not greater than about 50.

In many of the embodiments, the disclosed compounds have a normal boiling point as low as 20° C., 25° C., 45° C. or 50° C. or as high as 60° C., 70° C., 100° C. or 250° C., or within any range defined between any two of the foregoing values, such as from 20° C. to 70° C., from 45° C. to 60° C., or from 50° C. to 60° C., for example.

The disclosed compounds may also have no flash point as measured by one of the standard flash point methods, for example ASTM-1310-86 "Flash point of liquids by tag Open-cup apparatus" and an atmospheric lifetime of not greater than about 100 days, such as not greater than about 50 days. Further, the disclosed compound are miscible with greater than 20% by weight of mineral oil and/or silicone oil, such as in a weight ratio in the range of at least about 80:20 to about 20:80, or in substantially all proportions.

The disclosed compounds may exhibit a relatively low toxicity value.

As used herein, ODP is defined in the "Scientific Assessment of Ozone Depletion, 2002", a report of the World Meteorological association, incorporated herein by reference. As used herein, GWP is defined relative to that of carbon dioxide and over a 100 year time horizon, and defined in the same reference as for the ODP mentioned above. As used herein, miscibility is measured in accordance with visual evaluation of phase formation or separation when two liquids are mixed together, as is known to those skilled in the art.

The disclosed compounds thus generally possess properties and characteristics that are highly desirable for use in connection with many different applications, including many different types of cleaning and contaminant removal applications.

For example, in cleaning applications, the disclosed compounds may be used in liquid compositions, either alone or with one or more co-solvents, as cleaning solvents for greases, oils, waxes and the like, for use in mechanical part cleaning, precision cleaning and/or electronics cleaning, such as cleaning electric motors, compressors, heavy metal parts, delicate precision metal parts, printed circuit boards, gyroscopes, guidance systems, aerospace and missile hardware, aluminum parts and the like. Other applications include degreasing, dry-cleaning, solvent etching, and as a solvent for aerosols or other sprayable compositions, as carrier solvents for lubricants, or other surface treatment applications.

For example, in degreasing operations, the disclosed compounds may be used as solvents in vapor degreasing methods, in which an article to be cleaned is exposed to a solvent vapor, preferably at or above room temperature, to remove grease or other contaminants from the surface of the article or alternatively, in liquid degreasing operations, in which an article to be cleaned is exposed to the solvent in liquid form by immersing the article in the liquid solvent, typically at an elevated temperature approaching the boiling point of the solvent.

In one particular application, the solvents disclosed herein may be formulated with other components, such as a $C_1$-$C_3$ alcohol and/or a $C_4$-$C_6$ hydrocarbon, to form a composition useful for removing ink or ink-based markings from the surfaces of articles of manufacture, such as optical lenses, electro-mechanical or electrical parts, before the parts are packaged and commercially sold without damaging the underlying surfaces of the articles themselves. The articles and their surfaces may be metal or metal-based, cellulose-based, silica-based, or made from a plastic polymeric material, and the solvents may be in the form of a liquid, aerosol and/or sprayable composition.

The disclosed compounds may also be used as a heat transfer medium, flame suppressing agent, or foam blowing agent, for example. In particular, the disclosed compounds may be used as heat transfer fluids in methods and systems for transferring heat, such as refrigerants used in refrigeration, air conditioning and heat pump systems, and well as fire suppressants, such as additives to reduce the flammability of fluids, and as components involved in the formation of foam, foam premixes, foam products and blowing agents for foams.

Further details regarding exemplary applications of the disclosed compounds are disclosed in U.S. Pat. No. 7,985,299, assigned to the assignee of the present invention, the entire disclosure of which is incorporated by reference herein.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method for producing a product according to one of formulas:

$$CF_3\text{—}CH_2\text{—}CHCl\text{—}O\text{—}C_nH_xF_yCl_z \text{ and}$$

$$CF_3\text{—}CH\text{=}CH\text{—}O\text{—}C_nH_xF_yCl_z$$

wherein:
n is 1 to 5;
x, y, and z are each 0 to 11 and y+z≥1; and
x+y+z=2(n−m)+1, wherein m is an integer of 0 to 2, said method comprising the step of reacting a reaction mixture including an alcohol, a catalyst, and 1-chloro-3,3,3-trifluoro-propene (1233zd).

2. The method of claim 1, wherein the alcohol is an alcohol according to the following formula:

$$C_nH_xF_yCl_zOH$$

wherein:
n is 1 to 5;
x, y, and z are each 0 to 11 and y+z≥1; and
x+y+z=2n+1 for a saturated alcohol; or
x+y+z=2n−1 for an unsaturated alcohol.

3. The method of claim 2, wherein the alcohol is selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

4. The method of claim 1, wherein the catalyst is an alkaline catalyst.

5. The method of claim 4, wherein the catalyst is at least one alkali hydroxide selected from the group consisting of sodium hydroxide and potassium hydroxide and a combination thereof.

6. The method of claim 1, further comprising, after said reacting step, the additional step of separating the product of from the reaction mixture.

7. The method of claim 1, wherein said reacting step further comprises heating the reaction mixture.

8. The method of claim 1, wherein said reacting step further comprising the additional steps of:
mixing the alcohol and the catalyst in a reaction vessel; and
after said mixing step, adding 1-chloro-3,3,3-trifluoro-propene (1233zd) to the reaction vessel.

9. The method of claim 1, wherein the 1-chloro-3,3,3-trifluoro-propene (1233zd) is the trans isomer of 1-chloro-3,3,3-trifluoro-propene (1233zd).

10. The method of claim 1, wherein the 1-chloro-3,3,3-trifluoro-propene (1233zd) is the cis isomer of 1-chloro-3,3,3-trifluoro-propene (1233zd).

11. The method of claim 1, wherein the product has the following formula:

$$CF_3\text{—}CH_2\text{—}CHCl\text{—}O\text{—}C_nH_xF_yCl_z$$

wherein:
n is 1 to 5;
x, y, and z are each 0 to 11 and y+z≥1; and
x+y+z=2(n−m)+1, wherein m is an integer of 0 to 2, said method comprising the step of reacting a reaction mixture including an alcohol, a catalyst, and 1-chloro-3,3,3-trifluoro-propene (1233zd).

12. The method of claim 11, wherein the alcohol is an alcohol according to the following formula:

$$C_nH_xF_yCl_zOH$$

wherein:
n is 1 to 5;
x, y, and z are each 0 to 11 and y+z 1; and
x+y+z=2n+1 for a saturated alcohol; or
x+y+z=2n−1 for an unsaturated alcohol.

13. The method of claim 12, wherein the alcohol is selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

14. The method of claim 1, wherein the product has the following formula:

$$CF_3\text{—}CH\text{=}CH\text{—}O\text{—}C_nH_xF_yCl_z$$

wherein:
n is 1 to 5;
x, y, and z are each 0 to 11 and y+z≥1; and
x+y+z=2(n−m)+1, wherein m is an integer of 0 to 2, said method comprising the step of reacting a reaction mixture including an alcohol, a catalyst, and 1-chloro-3,3,3-trifluoro-propene (1233zd).

15. The method of claim 14, wherein the alcohol is an alcohol according to the following formula:

$$C_nH_xF_yCl_zOH$$

wherein:
n is 1 to 5;
x, y, and z are each 0 to 11 and y+z≥1; and
x+y+z=2n+1 for a saturated alcohol; or
x+y+z=2n−1 for an unsaturated alcohol.

16. The method of claim 15, wherein the alcohol is selected from the group consisting of fluoromethanol, 2,2,2-trifluoroethanol, 3,3,3-trifluoro-1-propanol, 2,2,3,3-tetrafluoro-1-propanol, 2,2,3,3,4,4,5,5-octafluoropentanol, and 1,1,1,3,3,3-hexafluoro-propan-2-ol.

* * * * *